United States Patent [19]

Pigerol et al.

[11] 4,129,572

[45] *Dec. 12, 1978

[54] PHENYL-2 INDOLE DERIVATIVES

[75] Inventors: Charles Pigerol, Saint-Ouen; Paul de Cointet de Fillain; Yves Bazile, both of Sisteron, all of France

[73] Assignee: Labaz, Paris, France

[*] Notice: The portion of the term of this patent subsequent to May 17, 1994, has been disclaimed.

[21] Appl. No.: 812,253

[22] Filed: Jul. 1, 1977

[30] Foreign Application Priority Data

Jul. 15, 1976 [FR] France .............................. 76 21582

[51] Int. Cl.$^2$ ............................................ C07D 209/12
[52] U.S. Cl. ..................... 260/326.12 R; 260/45.8 N; 260/326.16
[58] Field of Search .................. 260/326.16, 326.12 R

[56] References Cited

U.S. PATENT DOCUMENTS 4,024,155   5/1977   Pigerol et al. ................. 260/326.16

OTHER PUBLICATIONS

Bruce C.A. 54, 9883-9884 (1960).

*Primary Examiner*—Raymond V. Rush
*Attorney, Agent, or Firm*—Mason, Kolehmainen, Rathburn & Wyss

[57] ABSTRACT

2-Phenyl-indole derivatives of the general formula:

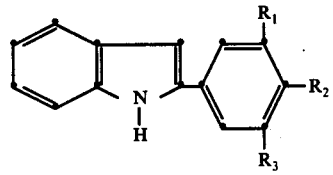

wherein $R_1$ represents a hydroxy radical, a branched- or straight-chain alkyloxy group containing from 1 to 12 carbon atoms, an allyloxy or propargyloxy radical, a cylcoalkyloxy radical containing from 5 to 7 carbon atoms or a benzyloxy radical, $R_2$ represents a hydroxy radical, an ethoxy, methylsulphonyloxy, benzenesulphonyloxy or toluenesulphonyloxy group and $R_3$ represents a hydrogen atom, a hydroxy radical or a methoxy group. The said 2-phenyl-indole derivatives are useful in particular as stabilizers of polymers and co-polymers of vinyl chloride.

5 Claims, No Drawings

PHENYL-2 INDOLE DERIVATIVES

This invention relates to 2-phenyl-indole derivatives and to processes for preparing the said 2-phenyl-indole derivatives.

The 2-phenyl-indole derivatives with which the invention is concerned are the substances represented by the formula:

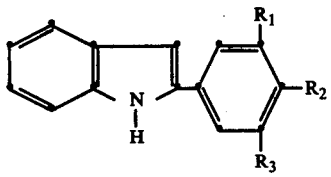

wherein $R_1$ represents a hydroxy radical, a branched- or straight-chain alkyloxy group containing from 1 to 12 carbon atoms, an allyloxy or propargyloxy radical, a cycloalkyloxy radical containing from 5 to 7 carbon atoms or a benzyloxy radical, $R_2$ represents a hydroxy radical, an ethoxy, methylsulphonyloxy, benzenesulphonyloxy or toluenesulphonyloxy group and $R_3$ represents a hydrogen atom, a hydroxy radical or a methoxy group.

The substances of formula I can be prepared, according to the FISCHER Indole Synthesis, by reacting a substituted acetophenone derivative, represented by the formula:

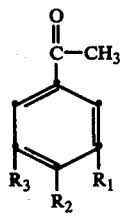

in which $R_1$, $R_2$ and $R_3$ have the same meanings as in formula I, with phenylhydrazine to form a substituted acetophenone phenylhydrazone, represented by the formula:

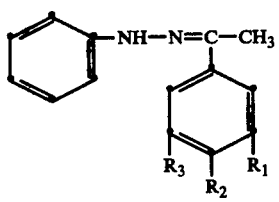

in which $R_1$, $R_2$ and $R_3$ have the same meanings as in formula I and cyclising the substances of formula III either with a dehydrating agent such as, for example, sulphuric acid, polyphosphoric acid or zinc chloride, or by thermolysis, to form the required 2-phenyl-indole derivative of formula I.

The substances of formula I may alternatively be prepared, according to the BISCHLER Indole Synthesis, by reacting a substituted acetophenone derivative, represent by the formula:

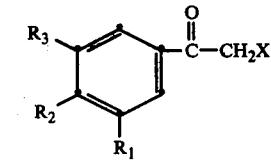

in which $R_1$, $R_2$ and $R_3$ have the same meanings as in formula I and X represents a halogen atom, preferably bromine or chlorine, with aniline to form the required 2-phenyl-indole derivative of formula I.

The substances of formula I wherein $R_1$ represent a hydroxy radical and $R_3$ a hydrogen atom or a hydroxy radical, may alternatively be prepared by demethylating the corresponding methoxy-substituted 2-phenyl-indole derivative, the said derivative having been prepared by one of the two general methods described above, by means of aluminium chloride or pyridine hydrochloride, optionally in the presence of benzene.

The compounds of formula I, wherein $R_2$ represents a hydroxy group, may alternatively be prepared by saponifying, in a alkaline medium, a compound of formula I, wherein $R_2$ represents a benzenesulphonyloxy group.

The substances of formula I, wherein $R_1$ represents an alkyloxy group and $R_3$ a hydrogen atom, may alternatively be prepared by reacting the corresponding hydroxylated 2-phenyl-indole derivative with an appropriate alkyl halide, in the presence of sodium hydride.

The substances of formula II are known or may be prepared by known procedures.

The substances of formula IV are either known or may be prepared by reacting the appropriate substance of formula II with a halogen, preferably bromine or chlorine.

The 2-phenyl-indole derivatives according to the invention which are listed hereunder have been found to be good stabilizers of polymers and co-polymers of vinyl chloride:

2-(3',5'-Dimethoxy-4'-hydroxy-phenyl)-indole (1)

2-(3'-Methoxy-4'-benzenesulphonyloxy-phenyl)-indole (2)

2-(3',5'-Dimethoxy-4'-benzenesulphonyloxy-phenyl)-indole (3)

2-(3'-Methoxy-4'-toluenesulphonyloxy-phenyl)-indole (4)

2-(3'-Methoxy-4'-methylsulphonyloxy-phenyl)-indole (5)

2-(3'-Hydroxy-4'-benzenesulphonyloxy-phenyl)-indole (6)

2-(3'-Butyloxy-4'-benzenesulphonyloxy-phenyl)-indole (7)

2-(3'-Isopropyloxy-4'-benzenesulphonyloxy-phenyl)-indole (8)

2-(3'-Allyloxy-4'-benzenesulphonyloxy-phenyl)-indole (9)

2-(3'-Propargyloxy-4'-benzenesulphonyloxy-phenyl)-indole (10)

2-(3'-Cyclohexyloxy-4'-benzenesulphonyloxy-phenyl)-indole (11)

2-(3'-n-Dodecyloxy-4'-benzenesulphonyloxy-phenyl)-indole (12)

2-(3'-Benzyloxy-4'-benzenesulphonyloxy-phenyl)-indole (13)

2-(3'-Hydroxy-4'-methylsulphonyloxy-phenyl)-indole (14)

2-(3',5'-Dihydroxy-4'-benzenesulphonyloxy-phenyl)-indole (15)
2-(3'-Propyloxy-4'-methylsulphonyloxy-phenyl)-indole (16)
2-(3'-Propyloxy-4'-hydroxy-phenyl)-indole (17)
2-(3'-Butyloxy-4'-hydroxy-phenyl)-indole (18)
2-(3'-Isopropyloxy-4'-hydroxy-phenyl)-indole (19)
2-(3'-Allyloxy-4'-hydroxy-phenyl)-indole (20)
2-(3'-Propargyloxy-4'-hydroxy-phenyl)-indole (21)
2-(3'-n-Dodecyloxy-4'-hydroxy-phenyl)-indole (22)
2-(3'-Benzyloxy-4'-hydroxy-phenyl)-indole (23)
2-(3'-Butyloxy-4'-ethoxy-phenyl)-indole (24)
2-(3'-Isopropyloxy-4'-ethoxy-phenyl)-indole (25)
2-(3'-Allyloxy-4'-ethoxy-phenyl)-indole (26)
2-(3'-n-Dodecyloxy-4'-ethoxy-phenyl)-indole (27)
2-(3'-Benzyloxy-4'-ethoxy-phenyl)-indole (28)

The stabilizers of the invention have been compared to 2-phenyl-indole which is one of the most valuable stabilizers used up to present.

The toxicity of the compounds of the invention was studied first and the satisfactory results obtained were such as to justify continuation of the investigation.

A. Acute toxicity

The maximal dose which did not provoke any deaths (LDO) amongst the experimental animals was determined and the following results were obtained:

| Compound | LDO (mg/kg) | Toxic symptoms |
|---|---|---|
| 2 | > 500 | none |
| 18 | > 500 | none |
| 19 | ≧ 1425 | none |
| 20 | ≧ 1400 | none |
| 21 | ≧ 1550 | none |
| 22 | ≧ 1500 | none |
| 23 | ≧ 1325 | none |
| 24 | ≧ 1475 | none |
| 25 | ≧ 1060 | none |
| 27 | ≧ 1400 | none |
| 28 | ≧ 1175 | none |

B. Thermostability of the stabilized resin

The stabilizing power of the substances of the invention was studied from two points of view: —Static thermostability —Dynamic thermostability (a) Static thermostability This study was carried out with the following formula of vinyl resin:

| Ingredient | Parts by weight |
|---|---|
| Polyvinyl chloride resin | 100 |
| Anti-shock resin | 9 |
| Epoxide soja bean oil | 2 |
| Calcium-12-hydroxy-stearate | 0.2 |
| SL 2016 | 0.1 |
| Stabilizer | 0.3 |

In the above formula, SL 2016 is a solution of zinc-2-ethylhexanoate in a mixture of hydrocarbons boiling between 158° C. and 184° C.

The results given hereunder were obtained by the method of GARDNER, which is described in U.S. Pat. No. 4,024,155, and working at a temperature of 185° C.

| Stabilizer | 0 | 6 | 12 | 18 | 24 | 30 | 36 | 42 | 48 | 54 | 60 |
|---|---|---|---|---|---|---|---|---|---|---|---|
| | | | | | Time in minutes | | | | | | |
| 1 | 1 | 1 | 2 | 4 | 9 | 10 | 11 | 11 | 12 | 14 | burnt |
| 19 | 1 | 1 | 1 | 2 | 2 | 3 | 4 | 6 | 8 | 11 | burnt |
| 22 | 1 | 1 | 2 | 2 | 3 | 4 | 5 | 7 | 9 | 11 | burnt |
| 2-phenyl-indole | 1 | 1 | 3 | 5 | 11 | 11 | 13 | 13 | 14 | burnt | burnt |

Compounds 1, 19 and 22 were found to be markedly superior to 2-phenyl-indole after only 12 minutes.

The following results were obtained by the simplified version of the GARNER method, but working at a temperature of 210° C.

| Stabilizer | 0 | 3 | 6 | 9 | 12 | 5 | 18 |
|---|---|---|---|---|---|---|---|
| | | | Time in minutes | | | | |
| 1 | 1 | 1 | 2 | 3 | 8 | 12 | burnt |
| 2-phenyl-indole | 1 | 1 | 3 | 11 | 13 | 14 | burnt |
| 2 | 1 | 1 | 3 | 6 | 14 | 14 | burnt |
| 2-phenyl-indole | 1 | 1 | 3 | 6 | 14 | 14 | burnt |
| 3 | 1 | 1 | 2 | 3 | 4 | 11 | burnt |
| 2-phenyl-indole | 1 | 1 | 3 | 5 | 6 | 13 | burnt |
| 18 | 1 | 1 | 3 | 5 | 8 | 13 | 17 |
| 2-phenyl-indole | 1 | 1 | 3 | 10 | 12 | 13 | burnt |
| 19 | 1 | 1 | 1 | 3 | 9 | 13 | burnt |
| 2-phenyl-indole | 1 | 1 | 3 | 4 | 12 | 14 | burnt |
| 22 | 1 | 1 | 1 | 2 | 4 | 9 | 10 |
| 2-phenyl-indole | 1 | 1 | 2 | 10 | 10 | 11 | burnt |
| 23 | 1 | 1 | 2 | 4 | 5 | 10 | 12 |
| 24 | 1 | 1 | 2 | 4 | 11 | 11 | 12 |
| 25 | 1 | 1 | 1 | 3 | 3 | 10 | 11 |
| 27 | 1 | 1 | 1 | 3 | 4 | 10 | 11 |
| 2-phenyl-indole | 1 | 1 | 2 | 8 | 9 | 10 | burnt |
| 26 | 1 | 1 | 1 | 2 | 5 | 10 | 16 |
| 28 | 1 | 1 | 1 | 3 | 6 | 10 | 16 |
| 2-phenyl-indole | 1 | 1 | 2 | 5 | 9 | 12 | burnt |

In this test, only Compound 2 was found to be equivalent to 2-phenyl-indole, all the others being superior to this latter substance.

C. Study of the extractibility of the stabilizers

The stabilizers according to the invention may be used to stabilize polymers which are intended for the manufacture of packaging and containers for food and drink and it was therefore necessary, in spite of their low toxicity, to determine their extractibility by solvents simulating food and drink.

This study was carried out in accordance with the requirements of the Food and Drug Administration (USA), by following the method which is described in U.S. Pat. No. 4,024,155 and using the following resin:

| Ingredient | Parts by weight |
|---|---|
| Polyvinyl chloride resin | 100 |
| Anti-shock resin | 12 |
| Epoxide soja bean oil | 3 |
| Chelating agent 1832 | 0.25 |
| Solution of 2-ethyl-potassium-hexanoate containing 10% of potassium | 0.25 |
| Solid calcium-zinc stabilizer | 0.2 |
| Calcium stearate | 0.2 |
| Glyceryl hydroxystearate | 1 |
| Glyceryl trimontanate | 0.3 |
| Acrylic resin | 0.5 |
| Stabilizer | 0 or 0.3 |

In the table given hereunder, the results are expressed in μg per liter and the duration of extraction is indicated for each solvent.

| Solvent | Stabilizer | | |
|---|---|---|---|
| | 2-phenyl-indole | 22 | 27 | 28 |
| Water (10 days) 3% Aqueous solution | 40 | <3 | <3 | <3 |

-continued

| Solvent | Stabilizer | | | |
|---|---|---|---|---|
| | 2-phenyl-indole | 22 | 27 | 28 |
| of acetic acid (20 days) | <3 | <3 | <3 | <3 |
| Aqueous ethanol 50/50 (9 days) | 100 | <10 | <10 | <10 |
| Heptane (48 hours) | 875 | 175 | 175 | 175 |

These results show that stabilizers 22, 27, 28, i.e. 2-(3'-n-dodecyloxy-4'-hydroxy-phenyl)-indole, 2-(3'-n-dodecyloxy-4'-ethoxy-phenyl)-indole and 2-(3'-benzyloxy-4'-ethoxy-phenyl)-indole, are markedly less extractible than 2-phenyl-indole with regard to water, aqueous ethanol and heptane.

In the case of diluted acetic acid, the amounts extracted are the same in each case, but it is difficult to draw a conclusion because these amounts are below the sensitivity threshold of the method of assay.

The stabilizers covered by the invention may be incorporated into the thermoplastic material in the proportion of 0.1 part to 1 part by weight.

The following Examples provide a non-limitative illustration of the processes of preparation of the substances covered by the invention:

EXAMPLE 1

2-(3'-Methoxy-4'-benzenesulphonyloxy-phenyl)-indole (a) Preparation of 3-methoxy-4-benzenesulphonyloxy-acetophenone Into a reactor was introduced an aqueous solution containing 44g (1.1 mol) of sodium hydroxide and 166g (1 mol) of 3-methoxy-4-hydroxy acetophenone. The solution was heated to 40°-45° C. and 194g (1.1 mol) of benzene sulphochloride were added in 2 hours.

The acetophenone with formed precipitated, the reaction medium was allowed to cool and the precipitate was filtered off and washed with purified water to neutrality. The 3-methoxy-4-benzenesulphonyloxy-acetophenone obtained was dried and directly used for the following step.

Melting point: 88° C. Yield: 99%.

(b) Preparation of 3-methoxy-4-benzenesulphonyloxy-acetophenone-phenylhydrazone

Into a reactor, equipped with a Dean-Stark separator, were introduced 100 ml of benzene, 1 ml of acetic anhydride, 10.8g (0.1 mol) of phenylhydrazine and 30.6 g (0.1 mol) of 3-methoxy-4-benzenesulphonyloxy-acetophenone. The reaction medium was stired and refluxed for 1 hour.

The solution was concentrated under reduced pressure and the phenylhydrazone precipitated and was directly used for the following step.

Melting point: 136° C. Yield: 100%.

(c) Preparation of 2-(3'-methoxy-4'-benzenesulphonyloxy-phenyl)-indole

Into a reactor were introduced 100 g of polyphosphoric acid, prepared by mixing 6 parts of orthophosphoric acid and 4 part of phosphoric anhydride. The acid was heated to 100° C., while stirring, 20g (0.05 mol) of 3-methoxy-4-benzenesulphonyloxy-acetophenone phenylhydrazone were added in 15 minutes. Stirring and temperature were maintained for ½ hour and the reaction medium was allowed to cool to 80° C. and was poured into water. The indole derivative was extracted with ether and the ethereal phase was washed with water to neutrality, dried and concentrated under reduced pressure. The precipitate was filtered off and recrystallized from methanol to give 2-(3'-methoxy-4'-benzenesulphonyloxy-phenyl)-indole.

Melting point: 156° C. Yield: 75%.

EXAMPLE 2

2-(3',5'-Dimethoxy-4'-benzenesulphonyloxy-phenyl)-indole (a) Preparation of 3,5-dimethoxy-4-benzenesulphonyloxy-acetophenone Into a reactor were introduced 1 liter of 1,2-dichloroethane, 196g (1 mol) of 3,5-dimethoxy-4-hydroxy-acetophenone, 151.5g (1.5 mol) of triethylamine and the reaction medium was stirred until a homogeneous solution was obtained. While stirring, 265g (1.5 mol) of benzene sulphochloride were added in one hour. The reaction was exothermic and the temperature of the medium increased to 40° C. This latter temperature was maintained for one hour after the end of the operation of addition, and the mixture was then poured into water.

The 3,5-dimethoxy-4-benzenesulphonyloxy-acetophenone precipitated and was filtered out, washed with water to neutrality, washed with ether and finally dried.

The product obtained was directly used for the following step.

Melting point: 96° C. Yield: 99%.

(b) Preparation of 3,5-dimethoxy-4-benzenesulphonyloxy-acetophenone phenylhydrazone The 3,5-dimethoxy-4-benzenesulphonyloxy-acetophenone obtained as described above was reacted with phenylhydrazine following the procedure set out in Example 1b and 3,5-dimethoxy-4-benzenesulphonyloxy-acetophenone phenylhydrazone was obtained with a yield of 100% in crude product, which was recrystallized from methanol and directly used for the following step.

Melting point 168° C.

(c) Preparation of 2-(3',5'-dimethoxy-4'-benzenesulphonyloxy-phenyl)-indole

The 3,5-dimethoxy-4-benzenesulphonyloxy-acetophenone phenylhydrazone obtained was cyclised by following the procedure described in Example 1c but with a reaction period of 1 hour. After recrystallization from ethanol 2-(3',5'-dimethoxy-4'-benzenesulphonyloxy-phenyl)-indole was obtained with a yield of 71%. Melting point: 150° C.

EXAMPLE 3

2-(3'-Methoxy-4'-methylsulphonyloxy-phenyl)-indole (a) Preparation of 3-methoxy-4-methylsulphonyloxy-acetophenone While stirring, 498g (3 mols) of 3'-methoxy-4'-hydroxy-acetophenone were slowly introduced, in one operation, into a reactor containing 2.7 liters of water and 132g of sodium hydroxide. 378.2g (3.3 mols) of methane sulphochloride were then added in two hours and at a temperature of 20° C. Stirring was maintained for ½ hour and 36g of solid sodium hydroxide and 34g (0.3 mol) of methane sulphochloride were added. Stirring was maintained for one hour and the crystallized product was suction-filtered at room temperature and washed with water until elimination of the chloride ions. The product was dried under vacuum in an oven at 40° C. for 12 hours and 694g of 3-methoxy-4-methyl-sulphonyloxy-acetophenone were obtained.

Melting point: 90° C. Yield: 94%.

(b) Preparation of 3-methoxy-4-methylsulphonyloxy-acetophenone phenylhydrazone The 3-methoxy-4-methylsulphonyloxy-acetophenone phenylhydrazone was prepared as in Example 1b and was directly used for the following step.

(c) Preparation of 2-(3'-methoxy-4'-methylsulphonyloxy-phenyl)-indole

The 3-methoxy-4-methylsulphonyloxy-acetophenone phenylhydrazone obtained was cyclised as in Example 1c and recrystallized from methanol to give 2-(3'-methoxy-4'-methylsulphonyloxy-phenyl)-indole.

Melting point: 194° C. Yield: 70%.

EXAMPLE 4

2-(3'-Methoxy-4'-toluenesulphonyloxy-phenyl)-indole

(a) Preparation of 1-toluenesulphonyloxy-2-methoxy-4-(1',1'-dimethoxy-2'-chloroethyl)-benzene 240g (0.75 mol) of 3-methoxy-4-toluenesulphonyloxy-acetophenone, prepared as in Example 1a, were dissolved at a temperature of 64° C. in 1.03 litre of methanol and, as soon as the reaction medium was homogeneous, 58.5g (0.82 mol) of chlorine were added in 1½ hours, the temperature being maintained at 64°-65° C.

The reaction medium was cooled to 20° C. by means of a water-bath and the diacetal precipitated and was maintained at −10° C. for one hour. The product was suction-filtered and dried in a ventilated oven at 40° C. for 12 hours to give 194g of 1-toluenesulphonyloxy-2-methoxy-4-(1',1'-dimethoxy-2'-chloro-ethyl)-benzene.

(b) Preparation of 3-methoxy-4-toluenesulphonyloxy-ω-chloroacetophenone

Into a reactor were introduced 194g of the above acetal, 480 ml of water and 48 ml of 96% sulphuric acid and, while stirring, the reaction medium was refluxed and the methanol which formed was continuously distilled off until a constant temperature of about 100° C. was obtained. The molten product were washed with water at 90°-95° C. and the oily product was allowed to cool slowly to 20° C., while being vigorously stirred in water until precipitation. The precipitate was suction-filtered and dried for one night in a ventilated oven at 40° C. to give 171g of 3-methoxy-4-toluenesulphonyloxy-ω-chloroacetophenone.

Melting point: 110°-112° C. Yield: 64%.

(c) Preparation of 2-(3'-methoxy-4'-toluenesulphonyloxy-phenyl)-indole

In a 250 ml-reactor 32.55g (0.35 mol) of aniline were heated to 180° C. By means of a dropping-funnel were added in 30 minutes 35.5g (0.1 mol) of molten 3-methoxy-4-toluenesulphonyloxy-ω-chloroacetophenone and the water which formed was eliminated by distilling off the azeotrope water-aniline by means of a Dean-Stark separator. While stirring, the temperature was maintained at 185° C. for 15 minutes after the end of the operation of addition.

While stirring, the reaction medium was poured into a mixture of 125 ml of water and 25 ml of 36% hydrochloric acid. Stirring was maintained for 15 minutes and the indole derivative which precipitated was suction-filtered and washed with water. The product was triturated with 60 ml of methanol, was suction-filtered and dried to give 22g of 2-(3'-methoxy-4'-toluenesulphonyloxy-phenyl)-indole.

Melting point: 182° C. Yield: 55.5%.

EXAMPLE 5

2-(3',5'-Dimethoxy-4'-hydroxy-phenyl)-indole

Into a reactor were introduced 10 ml of water containing 4.8g of solid sodium hydroxide, 30 ml of methanol and 75.6g (0.02 mol) of 2-(3',5'-dimethoxy-4'-benzenesulphonyloxy-phenyl)-indole. The reaction medium was heated to 50°-55° C., was stirred for 1 hour and was poured into an aqueous solution of hydrochloric acid. The indole derivative was extracted with ether and the ethereal phase was washed with water to neutrality, dried, treated with charcoal and, finally concentrated under reduced pressure to give 2-(3',5'-dimethoxy-4'-hydroxy-phenyl)-indole which was recrystallized from a mixture of ethanol-acetone 60/40.

Melting point: 230° C. Yield: 80%.

EXAMPLE 6

2-(3'-Hydroxy-4'-benzenesulphonyloxy-phenyl)-indole

Into a reactor equipped with a distillation column were introduced 700g (6.1 mol) of pyridine hydrochloride which was heated to 210° C. until elimination of the traces of water.

The reaction medium was cooled to 180° C. and 250g (0.66 mol) of 2-(3'-methoxy-4'-benzenesulphonyloxy-phenyl)-indole, prepared as in Example 1, were added.

The temperature dropped to 165°-167° C. and, while stirring, this latter was maintained for 3 hours.

The reaction medium was allowed to cool to 80° C. and was poured into water. The indole derivative was extracted with ether and the ethereal phase was washed with water, dried over anhydrous sodium sulphate and concentrated under reduced pressure.

The crude product obtained was purified by chromatography on a silica column, with 1,2-dichloro-ethane was eluent, to give 2-(3'-hydroxy-4'-benzenesulphonyloxy-phenyl)-indole.

Melting point: 158° C. Yield: 50-55%

By the same procedure, but using the appropriate starting-products, the following compounds were prepared:

| Compound | Melting Point |
|---|---|
| 2-(3'-Hydroxy-4'-methylsulphonyloxy-phenyl)-indole | 175° C |
| 2-(3',5'-Dihydroxy-4'-benzenesulphonyloxy-phenyl)-indole | 182° C (1,2-dichloro-ethane/toluene 80–20) |

EXAMPLE 7

2-(3'-Butyloxy-4'-benzenesulphonyloxy-phenyl)-indole

Into a reactor were introduced 70 ml of N,N-dimethylformamide and 18.25g (0.05 mol) of 2(3'-hydroxy-4'-benzenesulphonyloxy-phenyl)-indole, prepared as in Example 6. The reaction medium was cooled to 10° C. and, while stirring and under nitrogen atmosphere, 2.5g (0.05 mol) of an oily suspension of 50% sodium hydride were added in 10 minutes. Stirring and temperature were maintained for 10 minutes and 6.75g (0.05 mole) of butyl bromide were introduced in 5 minutes. The temperature was allowed to increase gradually and the reaction medium was then heated to 50°–60° C. for 3 hours. The reaction medium was allowed to cool and was poured into an aqueous solution of hydrochloric acid. The indole derivative was extracted with ether and the ethereal phase was washed with water, dried and concentrated under reduced pressure. The crude product obtained was purified by chromatography on a silica column, with benzene as eluent, and, after recrystallization from toluene, 2-(3'-butyloxy-4'-benzenesulphonyloxy-phenyl)-2 indole was obtained with a yield of 55%.

Melting point: 118° C.

By the same procedure, but using the appropriate starting-products, the following compounds were prepared:

| Compound | Melting Point ° C |
|---|---|
| 2-(3'-Cyclohexyloxy-4'-benzenesulphonyloxy-phenyl)-indole | 147 |
| 2-(3'-Isopropyloxy-4'-benzenesulphonyloxy-phenyl)-indole | 129 |
| 2-(3'-Allyloxy-4'-benzenesulphonyloxy-phenyl)-indole | 119 |
| 2-(3'-Propargyloxy-4'-benzenesulphonyloxy-phenyl)-indole | 125 |
| 2-(3'-n-Dodecyloxy-4'-benzenesulphonyloxy-phenyl)-indole | oily, not crystallized |
| 2-(3'-Benzyloxy-4'-benzenesulphonyloxy-phenyl)-indole | 155 |
| 2-(3'-Propyloxy-4'-methylsulphonyloxy-phenyl)-indole | 145 |

EXAMPLE 8

2-(3'-Butyloxy-4'-hydroxy-phenyl)-indole

Into a reactor were introduced 50 ml of methanol and 4.6g (0.1 mol) of solid potassium hydroxide and the mixture was stirred until complete dissolution.

While stirring, 8.4g (0.02 mol) of 2-(3'-butyloxy-4'-benzenesulphonyloxy-phenyl)-indole, prepared as in Example 7, were added and the reaction medium was refluxed for 1 hour. The methanol was evaporated off under reduced pressure and the reaction medium was poured into an aqueous solution of hydrochloric acid.

The indole derivative was extracted with ether and the ethereal phase was washed with water to neutrality, dried and concentrated under reduced pressure.

The crude product was purified by chromatography on a silica column, with benzene as eluent, and recrystallized from toluene to give 2-(3'-butyloxy-4'-hydroxy-phenyl)-indole.

Melting point: 163° C. Yield: 70%.

By the same procedure, but using the appropriate starting-products, the following compounds were prepared:

| Compound | Melting Point ° C |
|---|---|
| 2-(3'-Isopropyloxy-4'-hydroxy-phenyl)-indole | 121 (toluene) |
| 2-(3'-Allyloxy-4'-hydroxy-phenyl)-indole | 157 (toluene) |
| 2-(3'-Propargyloxy-4'-hydroxy-phenyl)-indole | 175 (1,2-dichloroethane/toluene) |
| 2-(3'-n-Dodecyloxy-4'-hydroxy-phenyl)-indole | 110 (toluene) |
| 2-(3'-Benzyloxy-4'-hydroxy-phenyl)-indole | 175 (toluene) |
| 2-(3'-Propyloxy-4'-hydroxy-phenyl)-indole | 168 (1,2-dichloroethane/toluene) |

EXAMPLE 9

2-(3'-Butyloxy-4'-ethoxy-phenyl)-indole

Into a reactor were introduced 30 ml of N,N-dimethylformamide, 1.23g (0.22 mol) of potassium hydroxide and 5.62g (0.02 mol) of 2-(3'-butyloxy-4'-hydroxy-phenyl)-indole, prepared as in Example 8.

While stirring, the reaction medium was heated to 50° C. and 3.43g (0.022 mol) of ethyl iodide were added in one operation.

Stirring and temperature were maintained for 3 hours and the reaction medium was then poured into water.

The indole derivative was extracted with ether and the ethereal phase was washed with purified water to neutrality, dried and concentrated under reduced pressure. The crude product was purified by chromatography on a silica column, with a mixture of benzene and heptane 90/10 as eluent.

After recrystallization from a mixture of methanol and 1,2-dichloro-ethane, 2-(3'-butyloxy-4'-ethoxy-phenyl)-indole was obtained.

Melting point: 139° C. Yield: 40%.

By the same procedure, but using the appropriate starting-products, the following compounds were prepared:

| Compound | Melting Point ° C |
|---|---|
| 2-(3'-Isopropyloxy-4'-ethoxy-phenyl)-indole | 169 |
| 2-(3'-Allyloxy-4'-ethoxy-phenyl)-indole | 167 |
| 2-(3'-n-Dodecyloxy-4'-ethoxy-phenyl)-indole | 103–106 |
| 2-(3'-Benzyloxy-4'-ethoxy-phenyl)-indole | 149 |

We claim:

1. A compound of the formula:

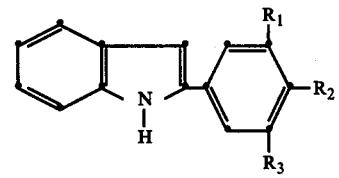

wherein $R_1$ represents a hydroxy radical, a branched- or straight-chain alkyloxy group containing from 1 to 12 carbon atoms, an allyloxy or propargyloxy radical, a cyclohexyloxy radical or a benzyloxy radical, $R_2$ represents a hydroxy radical, an ethoxy, methylsulphonyloxy, benzenesulphonyloxy or toluenesulphonyloxy group and $R_3$ represents a hydrogen atom, a hydroxy radical or a methoxy group, with the proviso that when $R_2$ represents a hydroxy or ethoxy group, $R_1$ represents allyloxy or propargyloxy.

2. 2-(3',5'-Dimethoxy-4'-benzenesulphonyloxy-phenyl)-indole.
3. 2-(3'-Allyloxy-4'-hydroxy-phenyl)-indole.
4. 2-(3'-Propargyloxy-4'-hydroxy-phenyl)-indole.
5. 2-(3'-Allyloxy-4'-ethoxy-phenyl)-indole.

* * * * *